(12) United States Patent
Zamyatin et al.

(10) Patent No.: US 8,724,876 B2
(45) Date of Patent: May 13, 2014

(54) METHOD AND SYSTEM FOR SUBSTANTIALLY REDUCING STREAK ARTIFACTS IN HELICAL CONE BEAM COMPUTER TOMOGRAPHY (CT)

(75) Inventors: Alexander Zamyatin, Hawthorn Woods, IL (US); Thomas Labno, Palatine, IL (US)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 61 days.

(21) Appl. No.: 13/275,814

(22) Filed: Oct. 18, 2011

(65) Prior Publication Data
US 2013/0094736 A1 Apr. 18, 2013

(51) Int. Cl.
*G06K 9/00* (2006.01)
*A61B 6/00* (2006.01)
*A61B 5/05* (2006.01)

(52) U.S. Cl.
USPC ............ 382/131; 378/4; 378/21; 600/425

(58) Field of Classification Search
USPC ........ 382/128–134; 378/4, 8, 15, 21–27, 101, 378/901; 600/407, 410, 425, 427, 411; 128/920, 922
See application file for complete search history.

(56) References Cited

U.S. PATENT DOCUMENTS

| | | | |
|---|---|---|---|
| 6,351,514 B1 * | 2/2002 | Besson | 378/15 |
| 6,463,118 B2 * | 10/2002 | Besson | 378/15 |
| 8,175,218 B2 * | 5/2012 | Hein et al. | 378/19 |
| 2009/0154639 A1 | 6/2009 | Nakanishi et al. | |

* cited by examiner

*Primary Examiner* — Abolfazl Tabatabai
(74) *Attorney, Agent, or Firm* — Yoshida & Associates, LLC

(57) ABSTRACT

Streak artifacts arise in helical CT reconstruction with cone beam weighting (CBW) with helical pitch ratio between 0.5 and 1.0 in a prevalent 2PI mode. The sreak artifacts are substantially removed by applying upsampling to the measured data in the segment direction before weighting. Furthermore, by making the upsampling adaptive to the view Z-position, an amount of extra processing is greatly reduced to near 1%.

22 Claims, 10 Drawing Sheets

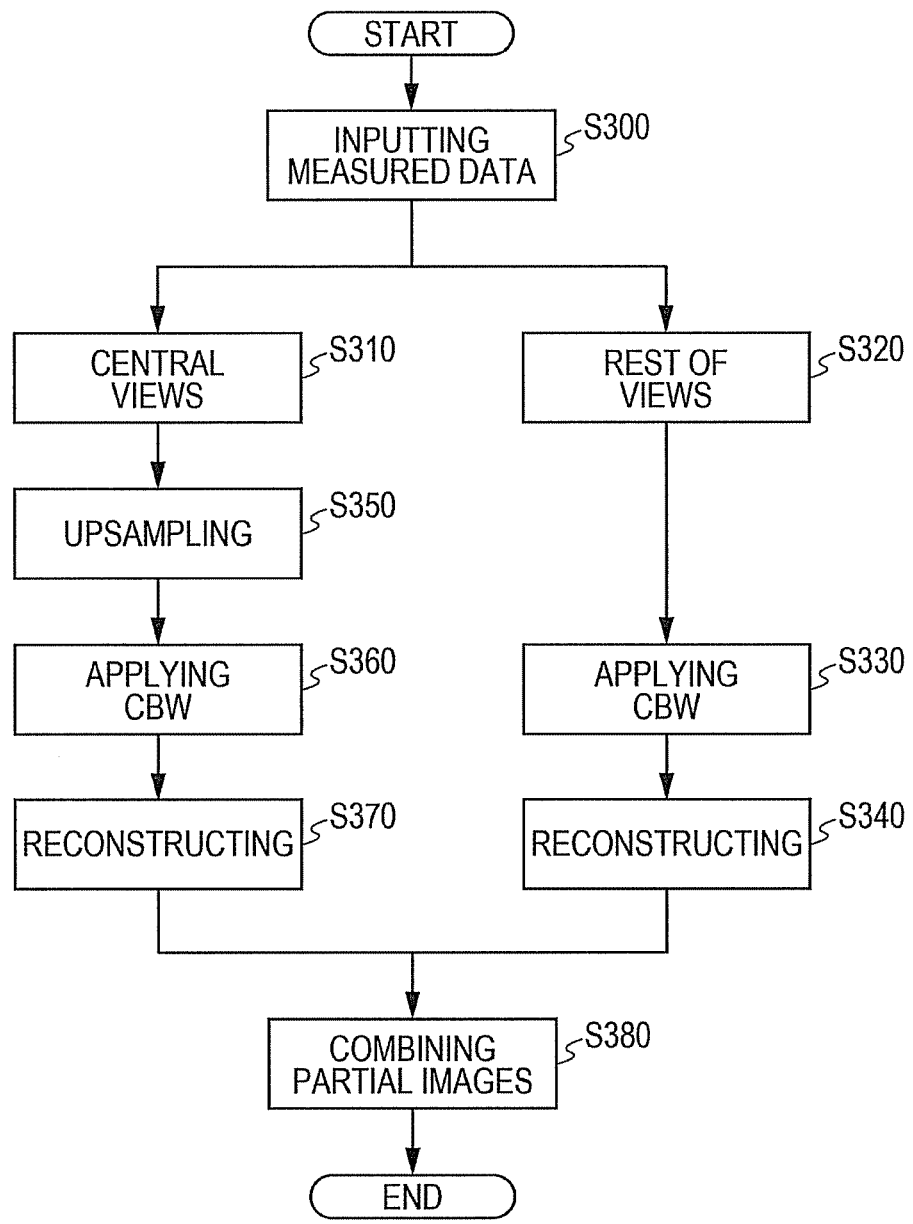

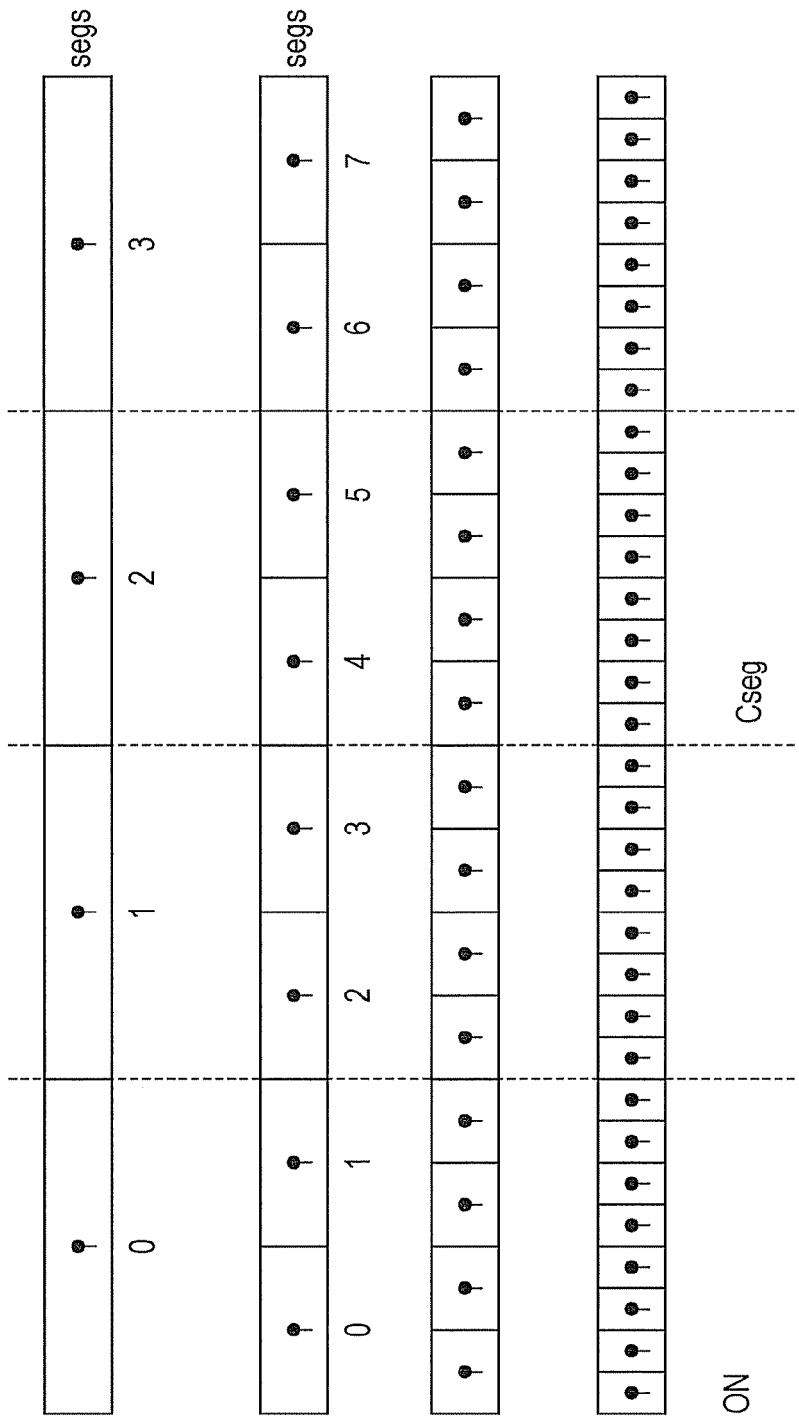

W/L=60/0
OBJECT: Z-UNIFORM CYLINDER

W/L=60/0
OBJECT: Z-UNIFORM CYLINDER

W/L=60/0
OBJECT: CLOCK PHANTOM

W/L=60/0
OBJECT: CLOCK PHANTOM

METHOD AND SYSTEM FOR SUBSTANTIALLY REDUCING STREAK ARTIFACTS IN HELICAL CONE BEAM COMPUTER TOMOGRAPHY (CT)

FIELD OF THE INVENTION

The current invention is generally related to an image processing and system, and more particularly related to substantially reducing streak artifacts in helical Cone Beam Computer Tomography (CT).

BACKGROUND OF THE INVENTION

Redundant data weighting is one of the significant steps in reconstructing images from helical cone beam data in computer tomography (CT). It affects various aspects including reconstruction accuracy, susceptibility to motion artifacts and noise. In prior art, cone beam weighting (CBW) is used in helical CT with a wide cone angle to reduce cone beam artifacts, to improve detector utilization and to reduce image noise. Prior art approaches usually consider a case of 1-PI reconstruction in which a view range is less than one rotation. However, the most practical helical CT in clinical settings uses the reconstruction view range between one and two rotations for each slice.

The CBW weight function such as uCBW can be implemented in several ways. In general, regardless of implementations, streak artifacts are caused by singularity of the CBW function at Z-positions near the image plane when the rotation is equal to or more than two. In particular, when an image plane projects to a small fraction of the detector row, and the non-linear form of uCBW cannot be accurately determined for all image pixels. In other words, a weight function generally becomes narrower than the detector size. Consequently, the inaccuracies in CBW weighting manifest themselves as streak artifacts.

In view of the above and other prior art problems, a desired streak artifact reduction technique is still desired to improve the image quality for helical cone beam CT.

BRIEF DESCRIPTION OF THE DRAWINGS

FIG. 5D is a flow chart illustrating overall steps involved in another exemplary streak artifact reduction process according to the current invention.

FIG. 6 is a diagram illustrating certain aspects of upsampling for substantially reducing streak artifacts by one embodiment according to the current inventions.

DETAILED DESCRIPTION OF THE EMBODIMENT(S)

Figure 1:
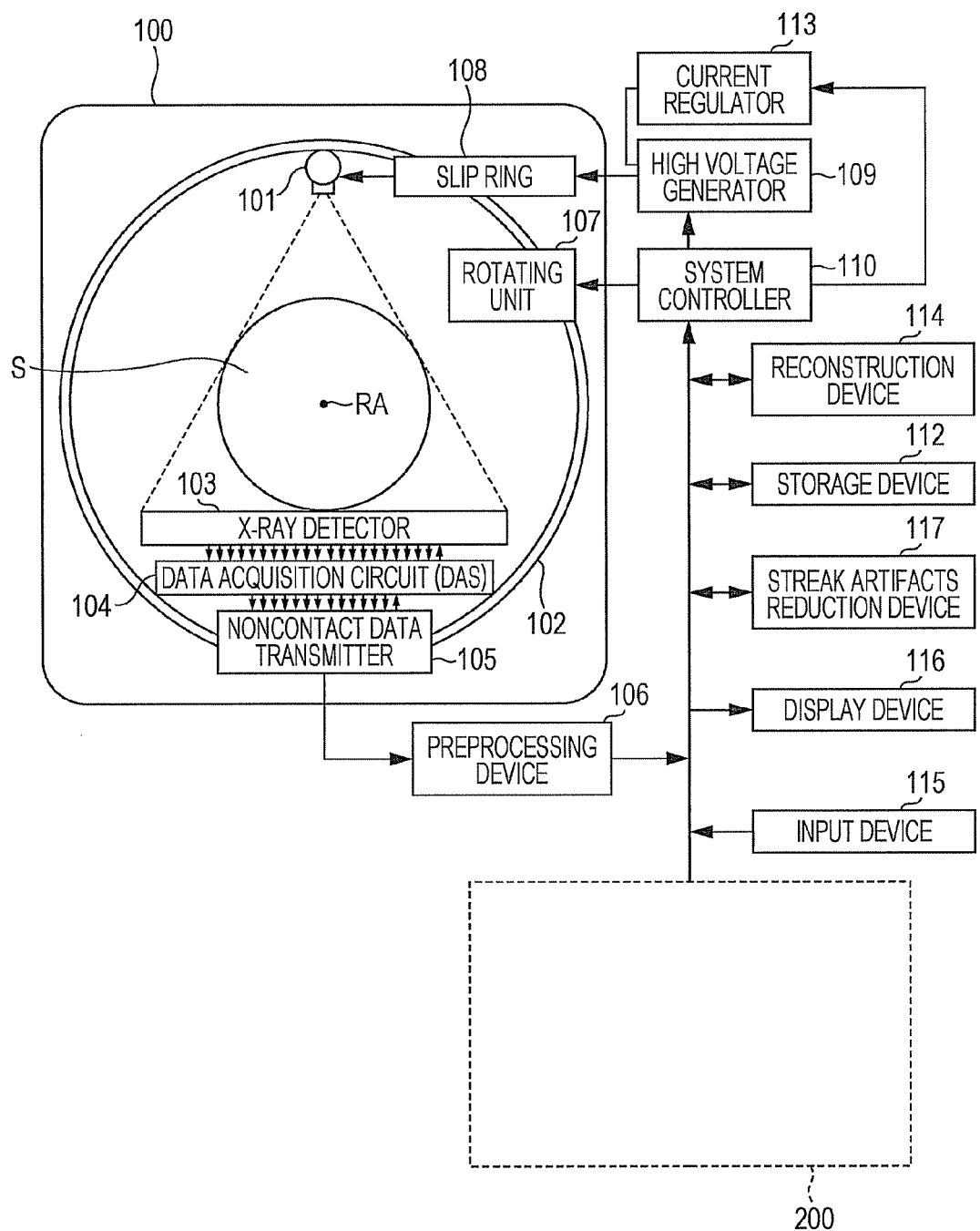
FIG. 1 is a diagram illustrating one embodiment of the multi-slice X-ray CT apparatus or scanner for substantially reducing streak artifacts according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116, multi-scale processing device 117 and the scan plan support apparatus 200. The scan plan support apparatus 200 includes a function for supporting an imaging technician to develop a scan plan.

One embodiment of the reconstruction device 114 further includes various software and hardware components and performs a predetermined analytic reconstruction process on the projection data. According to one aspect of the current invention, the reconstruction device 114 of the CT apparatus advantageously reconstructs an image volume by using a predetermined filtered backprojection (FBP) technique. The above described and other embodiments are optionally included in the current scope of the invention as more particularly claimed in the appended claims.

According to another aspect of the current invention, the reconstruction device 114 of the CT apparatus advantageously minimizes total variation (TV) using an iterative reconstruction technique. In general, the reconstruction device 114 in one embodiment of the current invention operates the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. The two steps are sequentially implemented in the main loop where a number of iterations were prescribed in one embodiment.

Before the TV minimization step, the projection data undergoes an ordered subsets simultaneous algebraic reconstruction technique (OS-SART). The projection data is grouped into a predetermined number of subsets N each having a certain number of views. During the ordered subsets simultaneous algebraic reconstruction technique (OS-SART), each subset may be sequentially processed in one embodiment. In another embodiment, a plurality of the subsets may be processed in parallel by taking advantage of certain microprocessor such as multiple central processing units (CPU) or a graphics processing unit (GPU). In the total variation (TV) minimization step, one embodiment of the reconstruction device 114 employs a line search strategy to search a positive step size so as to ensure the objective function of the current image volume to be smaller than that of the previous image volume.

During the ordered subsets simultaneous algebraic reconstruction technique (OS-SART), the reconstruction device 114 also performs two major operations. Namely, for each subset N, the reconstruction device 114 re-projects the image volume to form the computed projection data and back-projects the normalized difference between the measured projection and the computed projection data to reconstruct an updated image volume. In further detail, one embodiment of the reconstruction device 114 re-projects the image volume by using the ray tracing technique where no coefficient of the system matrix is cached. Moreover, one embodiment of the reconstruction device 114 simultaneously re-projects all rays in a subset, and this is optionally implemented in parallel. In the back-projection, one embodiment of the reconstruction device 114 uses a pixel-driven technique to back-project all of the normalized difference projection data in a subset to form the desired updated image volume. Because the reconstruction device 114 back-projects all ray sums, i.e., difference projection data, in a subset to form an image volume, this operation is optionally implemented in parallel too. These operations are applied to every subset N to complete a single OS-SART step. In addition, AWAD is optionally combined.

In addition to the above described components, one embodiment of the current invention further includes various other software modules and hardware components for performing streak artifact reduction. According to one aspect of the current invention, a streak artifact reduction device 117 of the CT apparatus advantageously performs streak artifact reduction functions for substantially reducing streak artifacts under certain situations. That is, a weight function such as a predetermined CBW function generally becomes narrower than the detector size for certain cone beam data as acquired over the helical source trajectory. Consequently, the inaccuracies in CBW weighting manifest themselves as streak artifacts. This problem will be further described with respect to other diagrams in the current application.

According to another aspect of the invention, one embodiment of the streak artifact reduction device 117 achieves a desired effect by upsampling the measured data for adding data values for hypothetical rows. The term, "upsampling" as used in the current application is well-known in the art and includes interpolation for adding additional data from the measured data. In other words, the embodiment upsamples the measured data to achieve a denser sampling level based upon numerically added data points. To add the upsampled data, the streak artifact reduction device 117 further determines an extent of its upsampling effect. For example, the streak artifact reduction device 117 determines a number of views against which upsampling takes place as well as a factor which limits the width in upsampling for adding a number of additional data points.

In one embodiment according to the current invention, the streak artifact reduction device 117 is operationally connected to other software modules and or system components such as the storage device 112, the reconstruction device 114, the display device 116 and the input device 115 via a data/control bus. In this regard, the streak artifact reduction device 117 alone does not necessarily perform the streak artifact functions and or their associated tasks in other embodiments according to the current invention. Furthermore, the streak artifact reduction device 117 is optionally a part of other devices such as the reconstruction device 114 in alternative embodiments according to the current invention.

Figure 2:
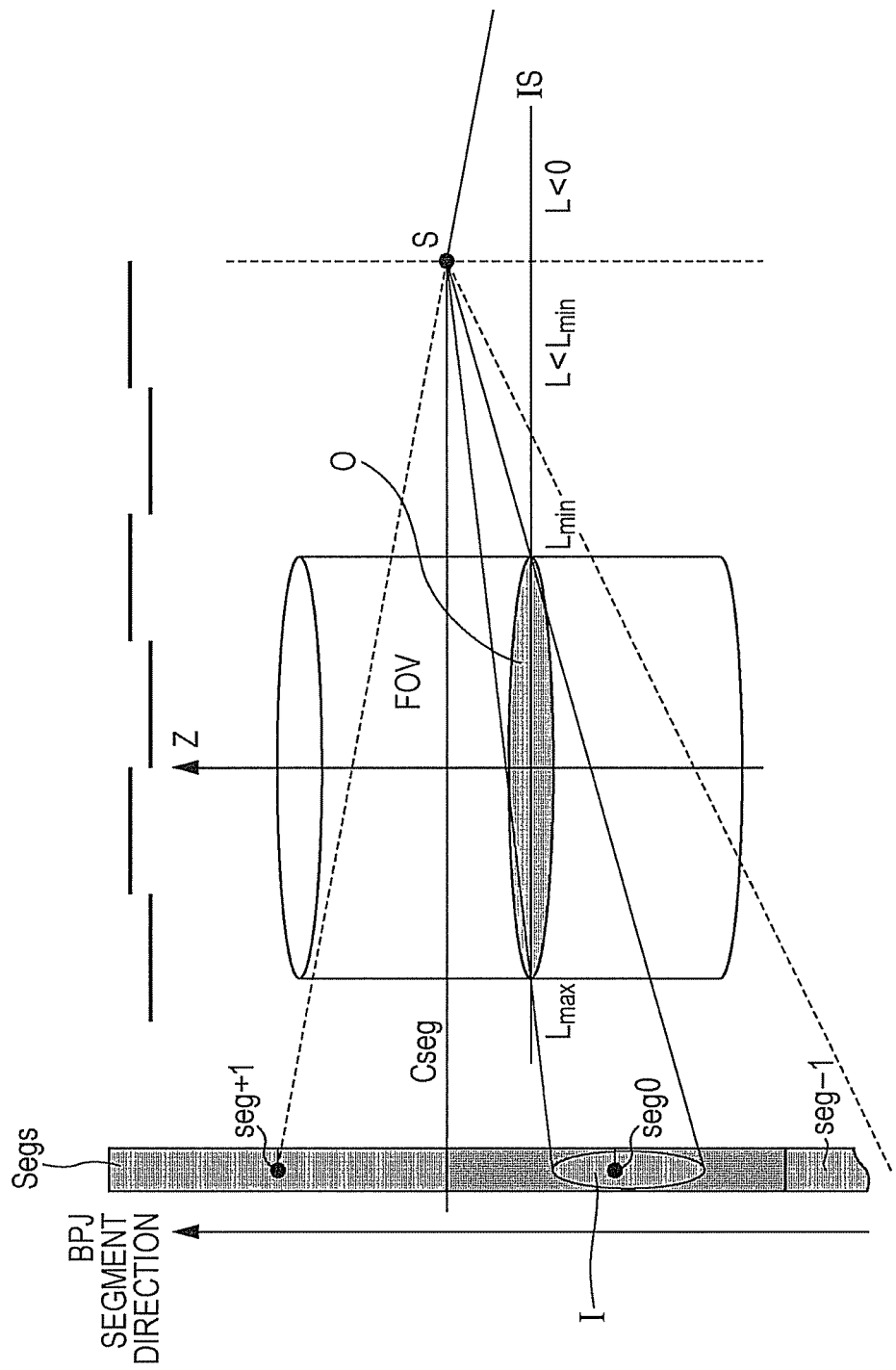
FIG. 2 is a diagram illustrating one aspect of the cause for streak artifacts to be substantially reduced by one embodiment according to the current inventions.

FIG. 2 is a diagram illustrating one aspect of the cause for streak artifacts to be substantially reduced by one embodiment according to the current inventions. The diagram illustrates an exemplary situation where a thin object O such as a heart is located at a relative position with respect to a source S over a predetermined helical trajectory. The exemplary situation also illustrates that the source position S is near an image slice IS for the object O. An image plane projects to a small fraction of a single detector row or segment seg0. Although a field of view (FOV) projects an image I of the object O onto the single segment seg0, a predetermined back projection (BPJ) technique requires for reconstruction a total of three BPJ segments including the middle segment seg0 and the adjacent segments seg+1 and seg−1. In the exemplary situation, the redundancy weighting such as a predetermined conebeam weighting (CBW) function becomes unstable at the adjacent segments seg+1 and seg−1. In general, the unstability is caused by the highly non-linear nature of the CBW function.

Figure 3A:
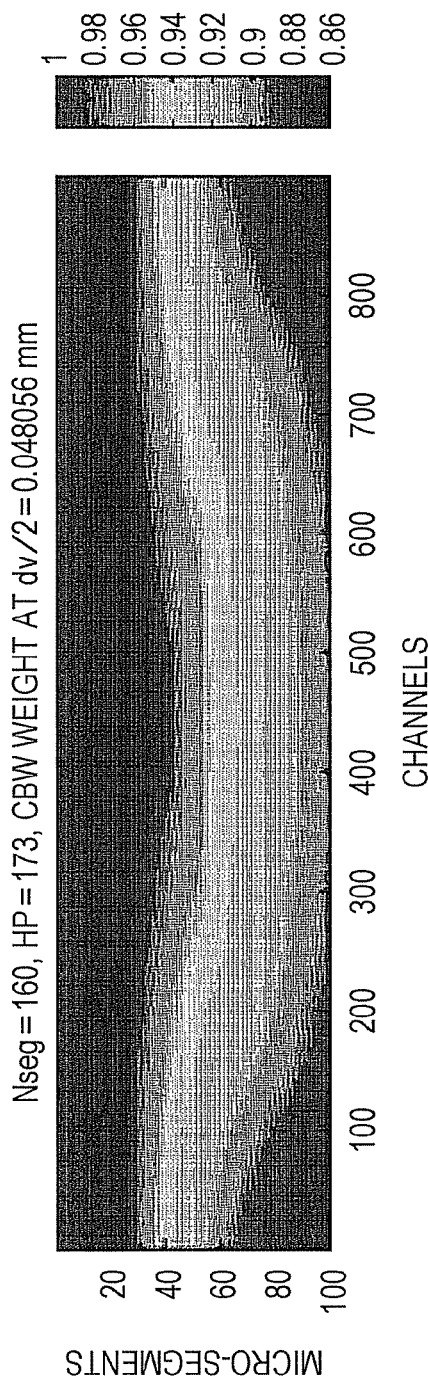
FIG. 3 illustrate a relationship between segments and one weight function in one embodiment of the multi-slice X-ray CT apparatus.
Figure 3C:
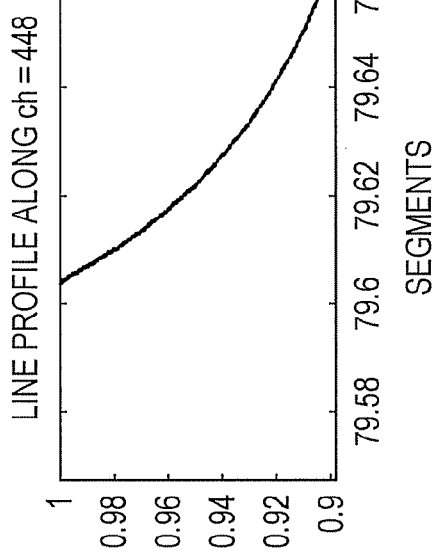
Figure 3B:
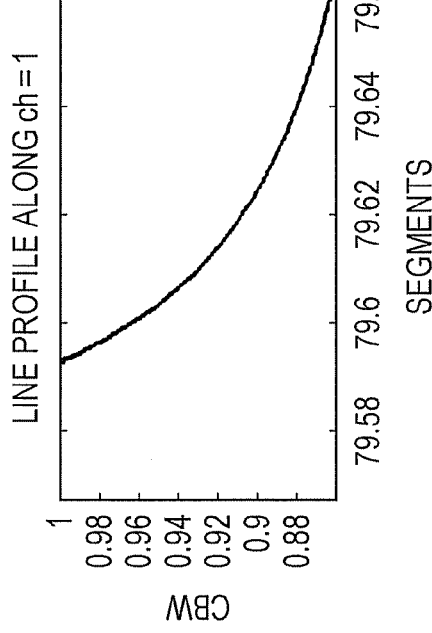

Now referring to FIGS. 3A, 3B and 3C, the diagrams illustrate a relationship between segments and one weight function in one embodiment of the multi-slice X-ray CT apparatus. FIG. 3A is a graph whose y axis indicates segments and x axis indicates channels or pixels. FIG. 3B is a graph indicating weights of a predetermined CBW function in the y axis and segments in the x axis. Between the segment values of 79.6 and 79.66, the CBW values drastically change for a line profile along a predetermined channel (ch=1) as illustrated in FIG. 3B. By the same token, FIG. 3C is a graph indicating weights of a predetermined CBW function in the y axis and segments in the x axis. Between the segment values of 79.6 and 79.66, the CBW values drastically change for a line profile along a predetermined channel (ch=448) as illustrated in FIG. 3C. Because of the highly non-linear nature of the CBW function over a narrow range of the segments, the CBW function cannot accurately weigh all image pixel values as shown in FIG. 3A.

Figure 4:
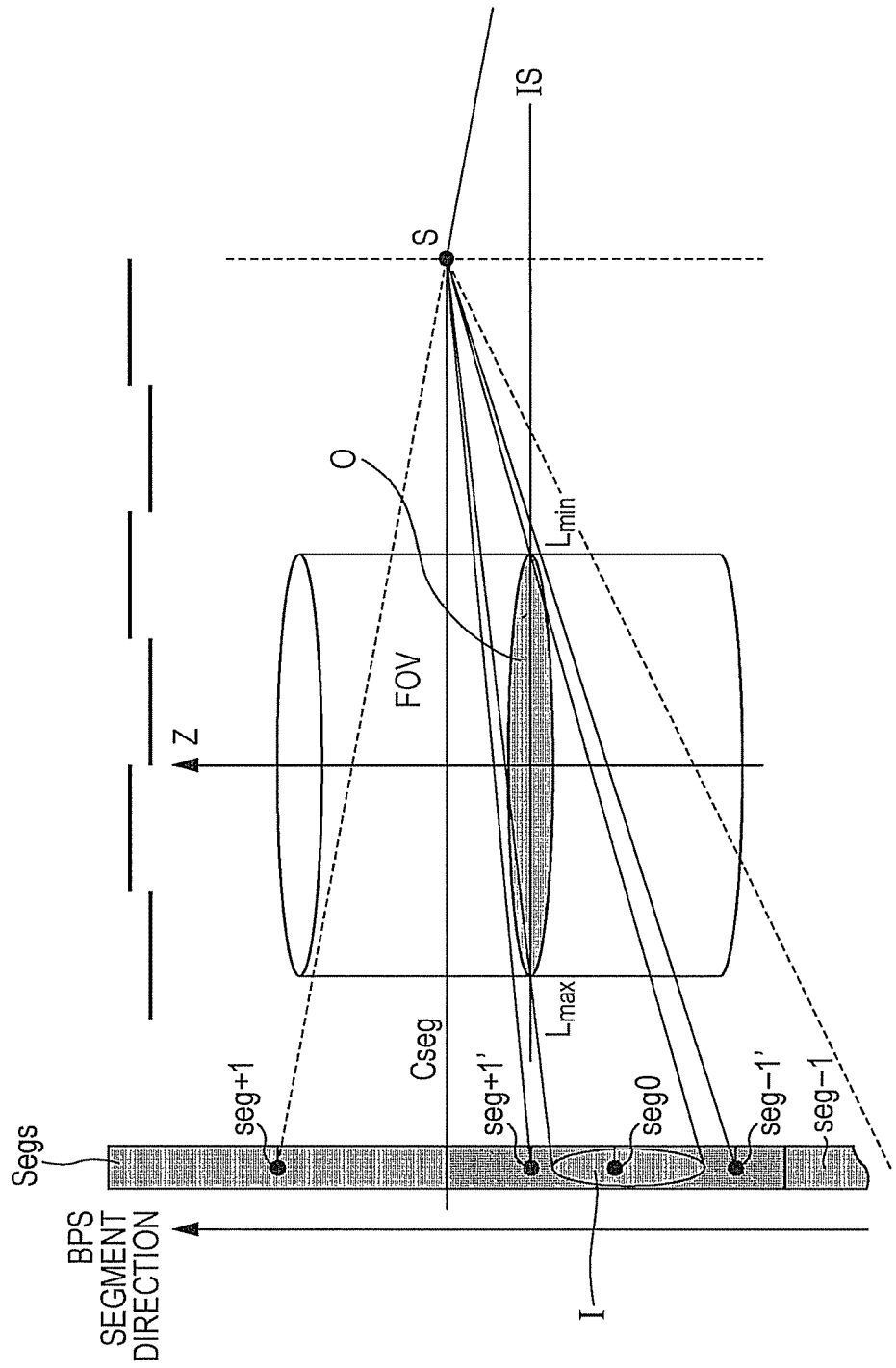
FIG. 4 is a diagram illustrating a certain solution for substantially reducing streak artifacts by one embodiment according to the current inventions.

FIG. 4 is a diagram illustrating a certain conceptual solution for substantially reducing streak artifacts by one embodiment according to the current inventions. As already described with respect to FIG. 2, an exemplary situation includes a thin object O such as a heart that is located at a relative position with respect to a source S over a predetermined helical trajectory. The exemplary situation also illustrates that the source position S is near an image slice IS for the object O. An image plane projects to a small fraction of a single detector row or segment seg0. Although a field of view (FOV) projects an image I of the object O onto the single segment seg0, a predetermined back projection (BPJ) technique requires for reconstruction a total of three BPJ segments including the middle segment seg0 and the adjacent segments seg+1 and seg−1. In the exemplary situation, the redundancy weighting such as using a predetermined conebeam weighting (CBW) function becomes unstable at the adjacent segments seg+1 and seg−1. In general, the unstability is caused by the highly non-linear nature of the CBW function as described with respect to FIGS. 3A, 3B and 3C. Consequently, the inaccuracies in CBW weighting manifest themselves as streak artifacts.

Still referring to FIG. 4, one exemplary solution for substantially reducing streak artifacts involves upsampling in one embodiment according to the current inventions. In the current exemplary embodiment, upsampling is optionally applied only near the above described image Z-position. That is, the newly generated data points by the upsampling operation are added near points seg+1' and seg−1' in the vicinity of the periphery of the image I on the segment seg0. Although the FOV still needs three segments during reconstruction, the weights by a predetermined function such as CBW are well defined for all segments due to additionally upsampled data points. The details of the upsampling operation will be further described with respect to the following flow charts and other diagrams in the current application.

Figure 5A:
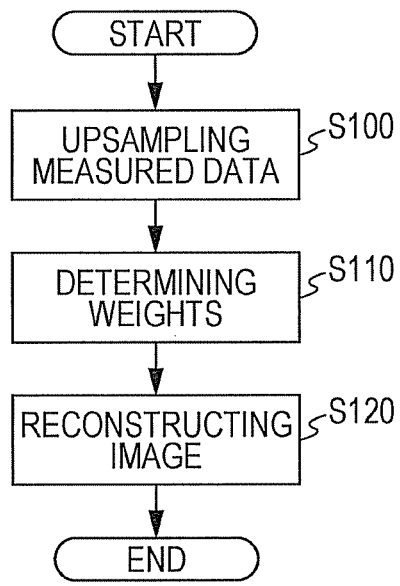
FIG. 5A is a flow chart illustrating general but core steps involved in the streak artifact reduction process in one embodiment according to the current invention.

FIG. 5A is a flow chart illustrating general steps involved in the streak artifact reduction process in one embodiment according to the current invention. In an exemplary process of substantially reducing streak artifacts, it is assumed that the measured data has been acquired by a predetermined helical data acquisition technique using a certain conebeam angle. In a step S100, the measured data is upsampled in the exemplary process of substantially reducing streak artifacts according to the current invention. Optionally, the upsampling step S100 determines which views to be upsampled. Furthermore, the upsampling step S100 also optionally determines how much to be upsampled. That is, the optional upsampling step S100 determines a number of additional data points to be interpolated from the existing measured data in one example. In one implementation, a value of a parameter such as "Ufactor" determines the interpolation characteristics. The upsampling step S100 is not limited to any particular technique, equation or manner to determine the above operational parameter values in order to practice the substantial streak artifact reduction according to the current invention.

The upsampling step S100 has additional determination with respect to its optimization of the streak artifact reduction process according to the current invention. For example, the number of views is related to optimization so that the exemplary streak reduction process according to the current invention does not have an unnecessarily large volume of data for achieving a certain level of improved image quality. In one implementation, the number of views is determined based upon a set of predetermined criteria or characteristics of the measure data. According to one aspect of the upsampling step S100, the number of views to be upsampled is fixedly determined for the entire measured data set. Alternatively, the above described number of views is optionally determined in an adaptive manner according to certain predetermined criteria or characteristics of the measure data. The upsampling step S100 is not limited to any particular technique, equation or manner to determine the above described operational manners in order to practice the substantial streak artifact reduction according to the current invention.

With the above described operational parameters, the upsampling step S100 in one embodiment actually generates additional data based upon the originally measured data according to the current invention. One exemplary technique of generating additional data is trilinear interpolation that is well known for upsampling. The upsampling step S100 is not limited to any particular technique or manner to add or interpolate data values based upon the originally measured data in order to practice the substantial streak artifact reduction according to the current invention.

After the upsampling step S100, a step 110 now determines redundancy weights according to a predetermined weight function such as CBW corresponding to the currently available data which includes the measured helical cone beam data and the interpolated data that has been obtained as a result of the above described upsampling operation. The weights are determined for all of the projection data prior to reconstruction in one exemplary process according to the current invention. Optionally, as the weights are determined, the currently available data is being weighted by applying the weights to generate weighted projection data. In another exemplary process according to the current invention, the weights are optionally determined as an image is being reconstructed.

Lastly, a step S120 now reconstructs an image based upon the previously determined data. In one exemplary reconstruction step of the step S120, an image is being reconstructed based upon the weighted projection data from the step S110. In another exemplary reconstruction step of the step S120, an image is being reconstructed based upon the currently available data and the corresponding weights from the step S110. Consequently, the reconstructed image includes a substantially reduced amount of the streak artifact. Furthermore, the streak artifact reduction process according to the current invention is not limited to any particular technique, equation, order or manner to reconstruct an image in order to practice the substantial streak artifact reduction according to the current invention.

Figure 5B:
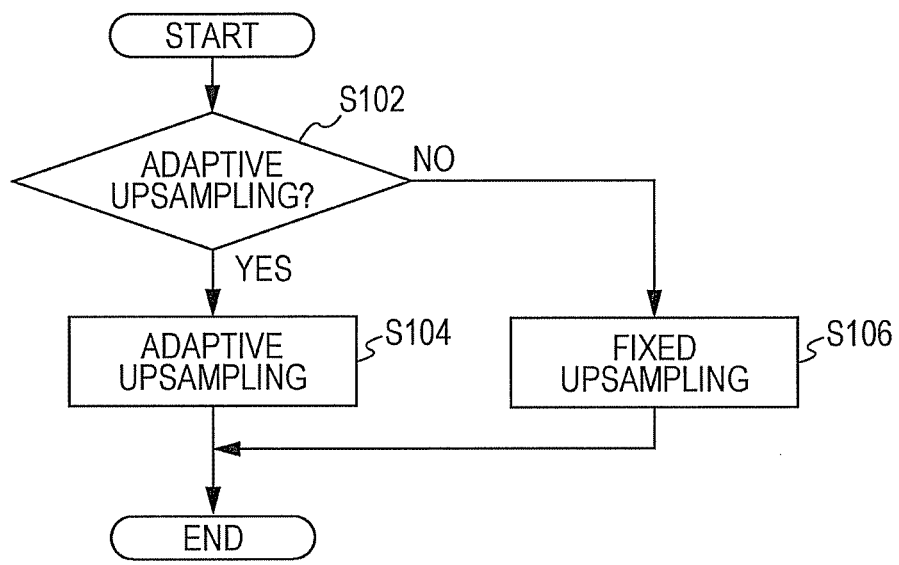
FIG. 5B is a flow chart illustrating a selection step for upsampling in the streak artifact reduction process in one embodiment according to the current invention.

FIG. 5B is a flow chart illustrating an optional selection step for upsampling in the streak artifact reduction process in one embodiment according to the current invention. A step S102 is performed in the above described upsampling step S100. The adaptive upsampling selection step S102 optionally determines as to whether or not the upsampling operation is performed in a predetermined adaptive manner. In one implementation, certain parameters are adaptively changed or fixed for the upsampling operation. For example, the parameters include a number of views to be upsampled and the width of interpolation for adding new data points. The interpolation width is also called Ufactor in the current application. If it is determined in the step S102 that the upsampling operation is not performed in an adaptive manner, the upsampling operation is performed for the entire measured data set with the fixed parameter values in one exemplary fixed upsampling step S106. Using the same example, the Ufactor is set to a single value regardless of a position of the current view to be upsampled.

Still referring to FIG. 5B, if it is determined in the step S102 that the upsampling operation is performed in an adaptive manner, the upsampling operation is performed on the measured data set with the variable parameter values in one exemplary adaptive upsampling step S104. Using the same example, a number of views is adaptively determined as Uview according to the following equation in one exemplary adaptive up sampling step S104.

$$Uview = 2 \times \text{ceil}\left((Tseg_{MIN} - 2)\frac{ViewRev}{HP}\right) \quad (1)$$

where ceil is a predetermined function, $Tseg_{MIN}$ is a minimal number of total segments to add, ViewRev is a number of views per revolution and HP is a helical pitch.

Furthermore, a range of the views for the upsampling operation is determined with respect to Uview. That is, where the views start and end for upsampling. Assuming that View Process is always even, the star and end views are respectively defined as Uview_start and Uview_end in teams of Uview in Equation (1) as follows:

$$Uview\_start = CentralView - \frac{Uview}{2} + 1/2 \quad (1A)$$

$$Uview\_end = CentralView - \frac{Uview}{2} - 1/2 \quad (1B)$$
$$= Uview\_start + Uview - 1$$

where $$CentralView = \frac{(View\ Process - 1)}{2}$$

and View Process is a umber of views to process in upsampling.

By the same token, the Ufactor is adaptively determined according to the following equation in one exemplary adaptive upsampling step S104.

$$U' = \left(\frac{(Tseg_{MIN} - 2)}{|\Delta view|} \times \frac{ViewRev}{HP}\right) \quad (2)$$

where $\Delta view$ is a distance from the central view, $Tseg_{MIN}$ is a minimal number of total segments to add, ViewRev is a number of views per revolution and HP is a helical pitch. Furthermore, $\Delta view$ is defined as $$\Delta view = view - \frac{View\ Process - 1}{2} \quad (3)$$

where ViewProcess is a umber of views to process in upsampling while view is a current view index ranging from 0 to ViewProcess−1.

In the above adaptive upsampling step S104, two exemplary aspects of the adaptive upsampling operation are illustrated in one embodiment according to the current invention. The adaptive upsampling parameters are not limited to these two exemplary aspects. In this regard, the adaptive upsampling step S104 is not limited to any particular technique, equation or manner to determine the above operational parameter values in order to practice the substantial streak artifact reduction according to the current invention.

Figure 5C:
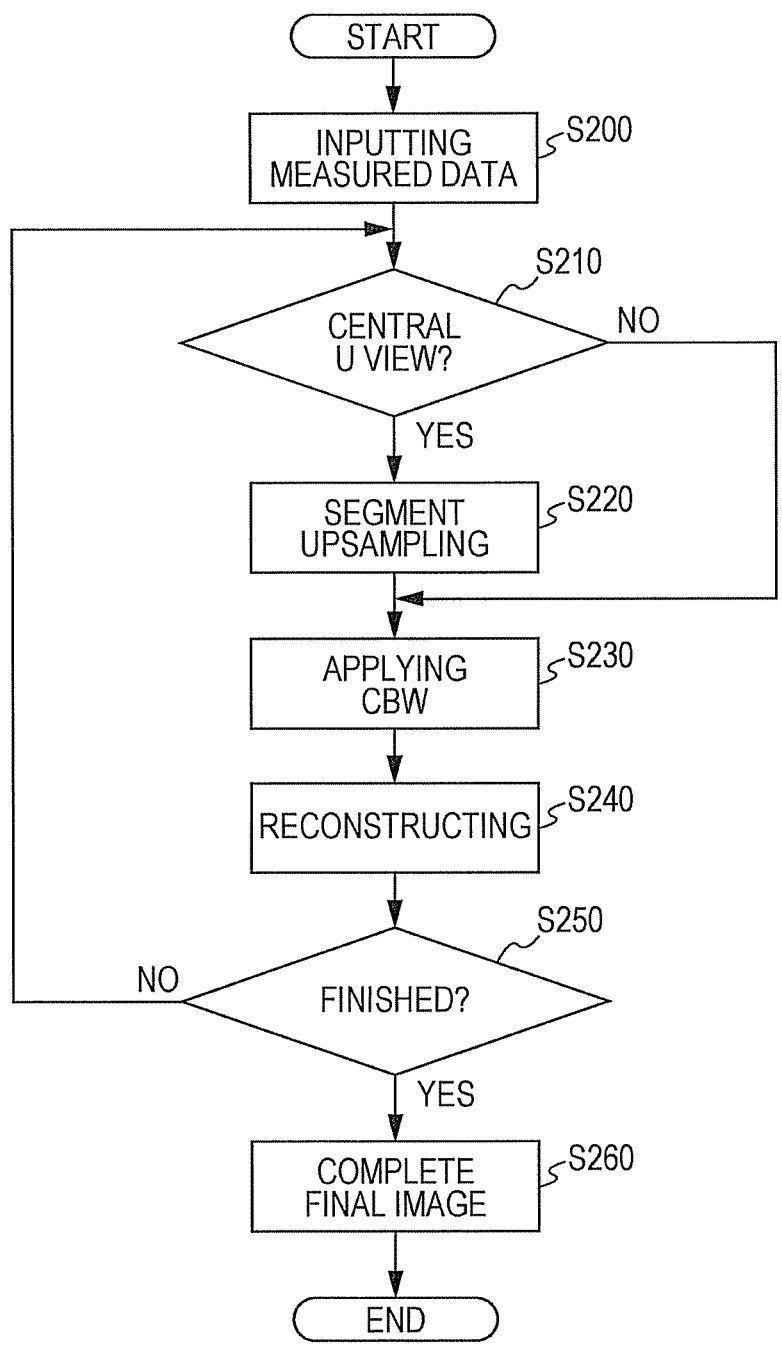
FIG. 5C is a flow chart illustrating overall steps involved in one exemplary streak artifact reduction process according to the current invention.

Now referring to FIG. 5C, a flow chart illustrates overall steps involved in one exemplary streak artifact reduction process according to the current invention. In this regard, some aspects of the upsampling operation as described with respect to FIGS. 5A and 5B are organized in a different manner in one embodiment of the streak artifact reduction process according to the current invention. In an exemplary process of substantially reducing streak artifacts, the measured data has been acquired by a predetermined helical data acquisition technique using a certain conebeam angle. In a step S200, the above measured data is inputted for further processing. In a step S210, it is determined as to whether or not a portion of the measured data belongs to a set of views to be upsampled. This determination is made in a variety of different ways. For example, Equations (1A) and (1B) are optionally used for the determination in the step S210. If it is determines in the step S210 that the view is not be upsampled, the exemplary process proceeds to a step S230. On the other hand, if it is determines in the step S210 that the view is to be upsampled, the exemplary process proceeds to a step S220, where the upsampling operation takes place to generate additional data points according to a predetermined technique such as interpolation.

Still referring to FIG. 5C, the step 230 determines redundancy weights according to a predetermined weight function such as CBW corresponding to the currently available data. In case the step S220 was performed, the currently available data includes the measured helical cone beam data and the interpolated data that has been obtained as a result of the above described upsampling operation. On the other hand, if the step S220 was not performed, the currently available data includes only the measured helical cone beam data. As the weight is determined, the currently available data is being weighted by applying the weight to generate weighted projection data. Subsequently, a step S240 now reconstructs an image based upon the previously determined data.

The above described steps 210 through 240 are repeated for the remaining portions of the measured data as determined in a step S250 as illustrated in FIG. 5. If the step S250 determines that all of the portions of the measured data have been processed, the exemplary process in a step S260 according to the current invention combines above reconstructed image portions from the step S240. Consequently, the combined reconstructed image includes a substantially reduced amount of the streak artifact.

The above described process of substantially reducing streak artifacts is optionally combine a set of other features as described with respect to other flow charts in FIGS. 5A, 5B and 5C. For example, the upsampling characteristics including a number of views such as uView and an interpolation width such as uFactor are optionally a combination of adaptive and fixed parameters. In any case, the streak artifact reduction process according to the current invention is not limited to any particular technique, equation, order or manner to reconstruct an image in order to practice the substantial streak artifact reduction according to the current invention.

Now referring to FIG. 5D, a flow chart illustrates overall steps involved in another exemplary streak artifact reduction process according to the current invention. In this regard, some aspects of the upsampling operation as described with respect to FIGS. 5A and 5B are organized in a different manner in this embodiment of the streak artifact reduction process according to the current invention. In an exemplary process of substantially reducing streak artifacts, the measured data has been acquired by a predetermined helical data acquisition technique using a certain conebeam angle. In a step S300, the above measured data is inputted for further processing. The measured data is split into two subsets including a first group of central views and a second group of the rest of the views. The central views are optionally defined by predetermined criteria and typically have a number of views ranging from 20 to 40. In general, the substantially streak artifact reducing process of the current invention processes the central views by upsampling them while the rest of the views without upsampling.

Still referring to FIG. 5D, the steps 310 through 370 process the central views. The step S310 selects the central views ranging from 20 to 40 in number. The central views are optionally selected by a combination of Equations (1), (1A) and (1B) in one embodiment according to the current invention. In the step S350, the upsampling operation is performed on the central views. The upsampling operation has a combinations of the features as described above with respect to FIGS. 5A through 5C. For example, the upsampling characteristics including a number of views such as uView and an intermpolation width such as uFactor are optionally a combination of adaptive and fixed parameters. The step S360 determines redundancy weights according to a predetermined weight function such as CBW corresponding to the currently available data on the central views. The currently available data includes the measured helical cone beam data and the interpolated data that has been obtained as a result of the above described upsampling operation. As the weight is determined, the currently available data is being weighted by applying the corresponding weight to generate weighted projection data. Subsequently, a step S370 now reconstructs an image based upon the previously determined data.

On the other hand, steps 320 through 340 process the rest of the views. For the rest of the views as selected in the step S320, no upsampling is performed. The exemplary process of the current invention processes the rest of the views by simply determining and or applying a weight in the step S330. Furthermore, the exemplary process of the current invention reconstructs an image in the step S340 based on the rest of the views after the step S330. Finally, the exemplary process in a step S380 according to the current invention combines above reconstructed image portions from the steps S340 and S370. Consequently, the combined reconstructed image includes a substantially reduced amount of the streak artifact.

As described above, the streak artifact reducing process carries out the predetermined operations on the central views in the steps S310 through S370 while the rest of the views in the steps 320 through 340 according to the current invention. In this regard, these steps may be sequential or parallel. One implementation of the streak artifact reducing process simultaneously operates on the central views and the rest of the views. That is, a first group of the steps S310 through S370 and a second group of the steps S320 through S340 are performed in parallel. In any case, the streak artifact reduction process according to the current invention is not limited to any particular technique, equation, order or manner to reconstruct an image in order to practice the substantial streak artifact reduction according to the current invention.

FIG. 6 is a diagram illustrating certain aspects of upsampling for substantially reducing streak artifacts by one embodiment according to the current inventions. One exemplary embodiment illustrates a relationship among a uFactor or U and a number of segments. Referring to FIG. 6A, at U=1, assuming there are four segments including segments 0 through 3, each segment has one data point as an example. FIG. 6B illustrates that at U=2, there are eight segments ranging from 0 through 7 as the number of segments is a product of a U value at the current level and the original number of segments at U=1. At U=2, each segment now has an additional data point that has been interpolated. By the same token, FIG. 6C illustrates that at U=4, there are sixteen segments ranging from 0 through 15 as the number of segments is a product of a U value at the current level and the original number of segments at U=1. At U=4, each segment now has three additional data points that have been interpolated. Lastly, FIG. 6D illustrates that at U=8, there are thirty-two segments ranging from 0 through 31 as the number of segments is a product of a U value at the current level and the original number of segments at U=1. At U=8, each segment now has eight data points that have been interpolated. The above described relationship is merely illustrative, and the streak artifact reduction process according to the current invention is not limited by any particular technique, equation or manner of the illustrated example of upsampling.

Figure 7A:
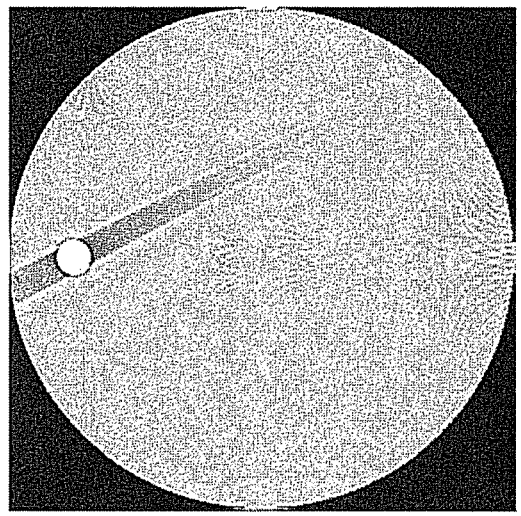
FIGS. 7A and 7B illustrate the effects of the substantial streak artifact reduction in one example comparison according to the current invention.
Figure 7B:
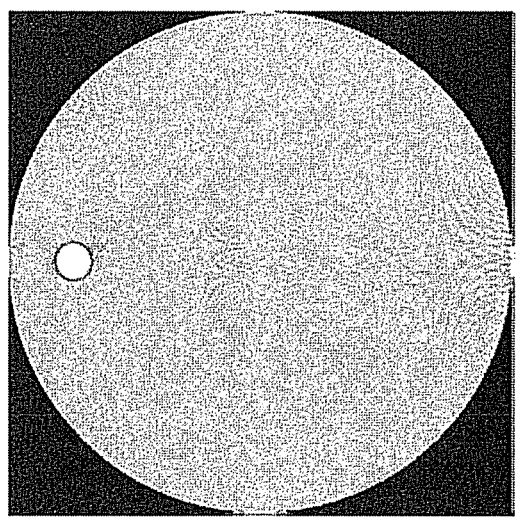

FIGS. 7A and 7B illustrate the effects of the substantial streak artifact reduction in one example comparison according to the current invention. FIG. 7A shows an image reconstructed from a Z-uniform cylinder without any correction on the streak artifact. A significant streak artifact is observed. FIG. 7B shows an image reconstructed from the Z-uniform cylinder with one exemplary process for substantially reducing the streak artifact according to the current invention. The significant streak artifact is substantially reduced.

Figure 8A:
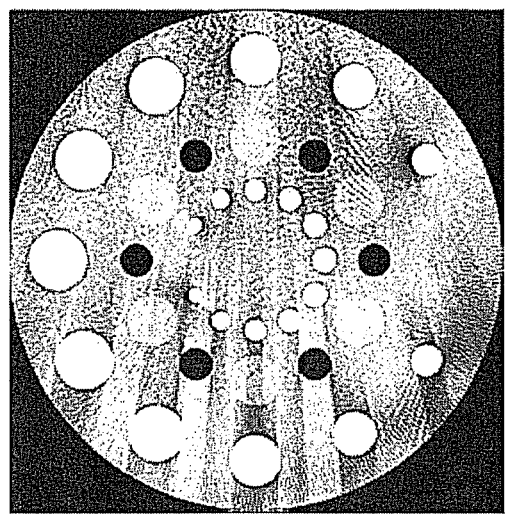
FIGS. 8A and 8B illustrate the effects of the substantial streak artifact reduction in another example comparison according to the current invention.
Figure 8B:
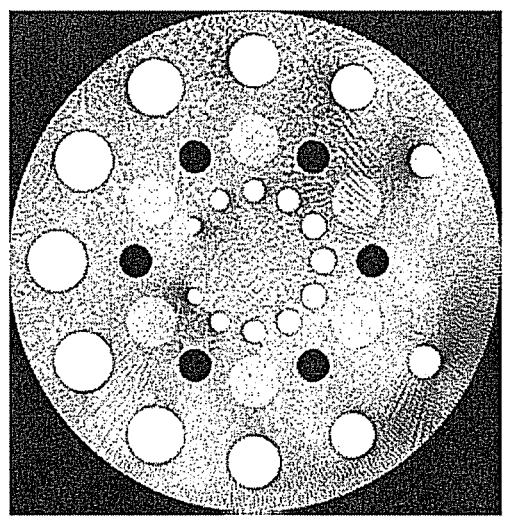

FIGS. 8A and 8B illustrate the effects of the substantial streak artifact reduction in another example comparison according to the current invention. FIG. 8A shows an image reconstructed from a clock phantom without any correction on the streak artifact. Some significant streak artifacts are observed. FIG. 8B shows an image reconstructed from the clock phantom with one exemplary process for substantially reducing the streak artifact according to the current invention. The significant streak artifacts are substantially reduced.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of weighting measured helical cone beam data in computed tomography, comprising the steps of:
    a) upsampling the measured helical cone beam data in a segment direction to obtain interpolated data with a reduced sampling pitch near a predetermined segment;
    b) determining weights based upon a predetermined cone beam weight function corresponding to the measured helical cone beam data and the interpolated data; and
    c) reconstructing an image using the weights, the measured data and the interpolated data.

2. The method of weighting measured helical cone beam data in computed tomography according to claim 1 wherein the reconstruction is between one and two rotations.

3. The method of weighting measured helical beam data in computed tomography according to claim 1 wherein the upsampling is performed with a fixed upsampling factor.

4. The method of weighting measured helical cone beam data in computed tomography according to claim 1 wherein the upsampling is performed with an adaptive upsampling factor.

5. The method of weighting measured helical cone beam data in computed tomography according to claim 4 wherein the adaptive upsampling factor depends on a view position.

6. The method of weighting measured helical cone beam data in computed tomography according to claim 5 wherein a number of the segments to be processed during the reconstruction is relatively constant.

7. The method of weighting measured helical cone beam data in computed tomography according to claim 5 wherein the adaptive upsampling factor U' is determined by $$U' = \left( \frac{(Tseg_{MIN} - 2)}{|\Delta view|} \times \frac{ViewRev}{HP} \right)$$

where $\Delta view$ is a distance from the central view, $Tseg_{MIN}$ is a minimal number of total segments to add, ViewRev is a number of views per revolution and HP is a helical pitch.

8. The method of weighting measured helical cone beam data in computed tomography according to claim 1 wherein the upsampling is performed in a fixed number of views.

9. The method of weighting measured helical cone beam data in computed tomography according to claim 1 wherein the upsampling is performed in an adaptive number of views (view positions).

10. The method of weighting measured helical cone beam data in computed tomography according to claim 9 wherein the adaptive number of views Uview is determined by $$Uview = 2 \times \text{ceil}\left( (Tseg_{MIN} - 2) \frac{ViewRev}{HP} \right)$$

where ceil is a predetermined function, $Tseg_{MIN}$ is a minimal number of total segments to add, ViewRev is a number of views per revolution and HP is a helical pitch.

11. The method of weighting measured helical cone beam data in computed tomography according to claim 1 wherein the predetermined cone beam weight function is $W_{CBW}$, which is a non-linear function as defined by $$W_{CBW}(\beta, \gamma, v) = \frac{u_{CBW}(\beta, \gamma, v)}{\sum_{n=-N}^{n=N} u_{CBW}(\beta_n^C(\beta, \gamma), \gamma_n^C(\gamma), v_n^C(\gamma, v))}$$

wherein $\beta$ is the view angle, $(\gamma, v)$ are the detector coordinates respectively in fan angle and vertical coordinates, and superscript C stands for complementary.

12. A system for weighting measured helical cone beam data in computed tomography, comprising:
an upsampling unit for upsampling the measured helical cone beam data in a segment direction to obtain interpolated data with a reduced sampling pitch near a predetermined segment;
a weight determining unit connected to said upsampling unit for determining weights based upon a predetermined cone beam weight function corresponding to the measured helical cone beam data and the interpolated data; and
a reconstruction unit connected to said upsampling unit and said weight determining unit for reconstructing an image using the weights, the measured data and the interpolated data.

13. The system for weighting measured helical cone beam data in computed tomography according to claim 12 wherein the reconstruction is between one and two rotations.

14. The system for weighting measured helical beam data in computed tomography according to claim 12 wherein said upsampling unit utilizes a fixed upsampling factor.

15. The system for weighting measured helical cone beam data in computed tomography according to claim 12 wherein said upsampling unit utilizes an adaptive upsampling factor.

16. The system for weighting measured helical cone beam data in computed tomography according to claim 15 wherein the adaptive upsampling factor depends on a view position.

17. The system for weighting measured helical cone beam data in computed tomography according to claim 16 wherein a number of the segments to be processed during the reconstruction is relatively constant.

18. The system for weighting measured helical cone beam data in computed tomography according to claim 16 wherein the adaptive upsampling factor U' is determined by $$U' = \left( \frac{(Tseg_{MIN} - 2)}{|\Delta view|} \times \frac{ViewRev}{HP} \right)$$

where $\Delta view$ is a distance from the central view, $Tseg_{MIN}$ is a minimal number of total segments, ViewRev is a number of views per revolution and HP is a helical pitch.

19. The system for weighting measured helical cone beam data in computed tomography according to claim 12 wherein said upsampling unit utilizes a fixed number of views.

20. The system for weighting measured helical cone beam data in computed tomography according to claim 12 wherein said upsampling unit utilizes an adaptive number of views (view positions).

21. The system for weighting measured helical cone beam data in computed tomography according to claim 20 wherein the adaptive number of views Uview is determined by $$Uview = 2 \times \text{ceil}\left( (Tseg_{MIN} - 2) \frac{ViewRev}{HP} \right)$$

where ceil is a predetermined function, $Tseg_{MIN}$ is a minimal number of total segments, ViewRev is a number of views per revolution and HP is a helical pitch.

22. The system for weighting measured helical cone beam data in computed tomography according to claim 12 wherein the predetermined cone beam weight function is $W_{CBW}$, which is a non-linear function as defined by $$W_{CBW}(\beta, \gamma, v) = \frac{u_{CBW}(\beta, \gamma, v)}{\sum_{n=-N}^{n=N} u_{CBW}(\beta_n^C(\beta, \gamma), \gamma_n^C(\gamma), v_n^C(\gamma, v))}$$

wherein $\beta$ is the view angle, $(\gamma, v)$ are the detector coordinates respectively in fan angle and vertical coordinates, and superscript C stands for complementary.

* * * * *